United States Patent
Wham et al.

(10) Patent No.: US 11,045,247 B2
(45) Date of Patent: Jun. 29, 2021

(54) SYSTEMS AND METHODS FOR CONTROLLING ARCING

(71) Applicant: COVIDIEN LP, Mansfield, MA (US)

(72) Inventors: Robert H. Wham, Boulder, CO (US); William D. Faulkner, Boulder, CO (US); Donald L. Tonn, Superior, CO (US)

(73) Assignee: COVIDIEN LP, Mansfield, MA (US)

( * ) Notice: Subject to any disclaimer, the term of this patent is extended or adjusted under 35 U.S.C. 154(b) by 346 days.

(21) Appl. No.: 15/900,377

(22) Filed: Feb. 20, 2018

(65) Prior Publication Data
US 2019/0254736 A1 Aug. 22, 2019

(51) Int. Cl.
*A61B 18/12* (2006.01)
*A61B 18/00* (2006.01)

(52) U.S. Cl.
CPC ...... *A61B 18/1233* (2013.01); *A61B 18/1206* (2013.01); *A61B 2018/00642* (2013.01); (Continued)

(58) Field of Classification Search
CPC ............ A61B 18/1233; A61B 18/1206; A61B 2018/1213; A61B 2018/00892; A61B 2018/00875; A61B 2018/00827; A61B 2018/00708; A61B 2018/00642; A61B 2018/00702; A61B 2018/00648; A61B 2018/00666
(Continued)

(56) References Cited

U.S. PATENT DOCUMENTS 4,114,623 A 9/1978 Meinke et al.
5,370,645 A * 12/1994 Klicek ............... A61B 18/1206
606/35
(Continued)

FOREIGN PATENT DOCUMENTS

CN 204542358 U 8/2015
EP 2042116 A1 4/2009
(Continued)

OTHER PUBLICATIONS

Australian Examination Report issued in corresponding Appl. No. AU 2019200636 dated Jun. 21, 2019 (6 pages).
(Continued)

*Primary Examiner* — Linda C Dvorak
*Assistant Examiner* — Nils A Potter

(57) ABSTRACT

The present disclosure relates to electrosurgical systems and methods for controlling electrical treatment energy in connection with electrical arcs. A method in accordance with the present disclosure includes providing electrical treatment energy to an instrument based on an indicated electrical energy level, accessing voltage signal values over time relating to voltage of the electrical treatment energy and/or current signal values over time relating to current of the electrical treatment energy, determining whether an arc generated by the instrument is an arc to be maintained or an arc to be extinguished based on a threshold value and at least one of the voltage signal values or the current signal values, and controlling the electrical treatment energy based on determining that the arc is an arc to be extinguished.

18 Claims, 12 Drawing Sheets

(52) U.S. Cl.
CPC .............. *A61B 2018/00678* (2013.01); *A61B 2018/00708* (2013.01); *A61B 2018/00827* (2013.01); *A61B 2018/00875* (2013.01); *A61B 2018/00892* (2013.01); *A61B 2018/1213* (2013.01)

(58) Field of Classification Search
USPC .......................................................... 606/34
See application file for complete search history.

(56) References Cited

U.S. PATENT DOCUMENTS

| | | | | |
|---|---|---|---|---|
| 5,730,719 A * | 3/1998 | Edwards | ............ | A61B 18/1477 604/22 |
| 5,766,165 A * | 6/1998 | Gentelia | ............ | A61B 18/1233 606/34 |
| 6,093,186 A * | 7/2000 | Goble | ................ | A61B 18/1206 606/32 |
| 7,651,492 B2 | 1/2010 | Wham | | |
| 8,165,666 B1 * | 4/2012 | Briggs | ............... | A61B 5/02405 600/515 |
| 9,498,275 B2 | 11/2016 | Wham et al. | | |
| 2007/0250052 A1 * | 10/2007 | Wham | ............... | A61B 18/1206 606/34 |
| 2009/0270849 A1 * | 10/2009 | Truckai | ................ | A61B 18/042 606/13 |
| 2012/0083779 A1 * | 4/2012 | Hosier | ............... | A61B 18/1233 606/33 |
| 2012/0101413 A1 * | 4/2012 | Beetel | ................ | A61B 18/1492 601/3 |
| 2012/0271304 A1 * | 10/2012 | Werner | ............. | A61B 18/1233 606/45 |
| 2014/0276749 A1 * | 9/2014 | Johnson | ................ | A61B 18/18 606/33 |
| 2016/0022349 A1 | 1/2016 | Woloszko et al. | | |
| 2016/0038216 A1 | 2/2016 | Woo et al. | | |
| 2016/0113702 A1 | 4/2016 | Keller | | |
| 2016/0310202 A1 * | 10/2016 | Wham | ............... | A61B 18/1206 |
| 2017/0202607 A1 | 7/2017 | Shelton, IV et al. | | |
| 2018/0076725 A1 * | 3/2018 | Xue | ................. | H02M 3/33569 |

FOREIGN PATENT DOCUMENTS

| | | |
|---|---|---|
| EP | 2649956 A1 | 10/2013 |
| JP | 2009082707 A | 4/2009 |

OTHER PUBLICATIONS

Canadian Office Action issued in corresponding Appl. No. CA 3,031,744 dated Dec. 10, 2019 (7 pages).

Office Action issued in corresponding Japanese Appl. No. JP 2019-027261, together with English language translation, dated Jan. 10, 2020 (12 pages).

Extended European Search Report issued in corresponding Appl. No. EP 19157938.2 dated Jul. 3, 2019 (7 pages).

Japanese Office Action issued in corresponding Appl. No. JP 2019-027261 dated Aug. 27, 2020 (3 pages) together with English language translation (4 pages).

Office Action issued in corresponding Japanese Appl. No. 2019-027261 (2 pages) dated Feb. 19, 2021, together with English language translation (4 pages).

* cited by examiner

SYSTEMS AND METHODS FOR CONTROLLING ARCING

BACKGROUND

1. Technical Field

The present disclosure generally relates to electrosurgical generators. More particularly, the present disclosure relates to electrosurgical systems and methods for controlling electrical treatment energy in connection with electrical arcs.

2. Background of Related Art

An electrosurgical generator is used in surgical procedures to provide electrical energy for treating the tissue of a patient. When an electrosurgical probe or another electrosurgical instrument is connected to the generator, the instrument can be used for cutting, coagulation, sealing, or fulgurating patient tissue with high frequency electrical energy. During operation, electrical current from the generator is applied by an electrode of the instrument to tissue and bodily fluids of a patient.

In certain modes, the electrical energy provided by the electrosurgical generator enables the instrument to create electrical arcs, which are beneficial for certain procedures, such as fulguration of tissue. However, an electrical arc needs to be carefully controlled so that it achieves intended benefits without causing unintended harm. Therefore, it is desirable to control the electrical treatment energy provided by the electrosurgical generator when an electrical arc is detected. Accordingly, there is continued interest in developing and improving the control of electrical energy provided by an electrosurgical generator.

SUMMARY

The present disclosure relates to electrosurgical systems and methods for controlling electrical treatment energy in connection with electrical arcs. As will be described herein in more detail, when an electrosurgical generator provides electrical treatment energy to an instrument and determines that the instrument is creating an arc that should be extinguished, such as a sustained arc to metal, the electrosurgical generator controls the electrical treatment energy based on that determination.

In accordance with aspects of the present disclosure, the present disclosure includes a method for controlling electrical treatment energy provided to an instrument. The method includes providing electrical treatment energy to the instrument based on an indicated electrical energy level, accessing voltage signal values over time relating to voltage of the electrical treatment energy and/or current signal values over time relating to current of the electrical treatment energy, determining whether an arc generated by the instrument is an arc to be maintained or an arc to be extinguished based on a threshold value and at least one of: the voltage signal values or the current signal values, and controlling the electrical treatment energy based on determining that the arc is an arc to be extinguished.

In various embodiments, determining whether the arc is an arc to be maintained or an arc to be extinguished includes determining that the arc is an arc to be extinguished based on a magnitude of change in peak-to-peak voltage of the electrical treatment energy over time being greater than the threshold value, where the threshold value changes corresponding to changes in the indicated electrical energy level.

In various embodiments, determining whether the arc is an arc to be maintained or an arc to be extinguished includes determining that the arc is an arc to be extinguished based on a magnitude of change in peak-to-peak current of the electrical treatment energy over time being greater than the threshold value, where the threshold value changes corresponding to changes in the indicated electrical energy level.

In various embodiments, determining whether the arc is an arc to be maintained or an arc to be extinguished includes determining that the arc is an arc to be extinguished based on a normalized change in peak-to-peak voltage of the electrical treatment energy over time being greater than the threshold value. The normalized change in peak-to-peak voltage is a ratio of a magnitude of change in peak-to-peak voltage of the electrical treatment energy over one of: RMS voltage of the electrical treatment energy, RMS current of the electrical treatment energy, or average power of the electrical treatment energy. In this manner, the threshold value does not change for changes in the indicated electrical energy level.

In various embodiments, determining whether the arc is an arc to be maintained or an arc to be extinguished includes determining that the arc is an arc to be extinguished based on a normalized change in peak-to-peak current of the electrical treatment energy over time being greater than the threshold value. The normalized change in peak-to-peak current is a ratio of a magnitude of change in peak-to-peak current of the electrical treatment energy over one of: RMS voltage of the electrical treatment energy, RMS current of the electrical treatment energy, or average power of the electrical treatment energy. In this manner, the threshold value does not change for changes in the indicated electrical energy level.

In various embodiments, determining whether the arc is an arc to be maintained or an arc to be extinguished includes determining a peak-to-peak voltage at a first time as a difference between a positive voltage peak and a negative voltage peak of the electrical treatment energy at the first time, determining a peak-to-peak voltage at a second time as a difference between a positive voltage peak and a negative voltage peak of the electrical treatment energy at a second time, the second time being after the first time, determining a change in peak-to-peak voltage as an absolute value of a difference between the peak-to-peak voltage at the first time and the peak-to-peak voltage at the second time, determining an RMS voltage of the electrical treatment energy and an RMS current of the electrical treatment energy for the second time, determining a first normalized change in peak-to-peak voltage as a ratio of the change in peak-to-peak voltage over the RMS voltage, determining a second normalized change in peak-to-peak voltage as a ratio of the change in peak-to-peak voltage over the RMS current, accessing an impedance value indicative of an impedance of the arc, and determining that the arc is an arc to be extinguished when: the first normalized change in peak-to-peak voltage is greater than the threshold and the impedance value is less than a first impedance threshold, or the second normalized change in peak-to-peak voltage is greater than a second threshold and the impedance value is less than a second impedance threshold.

In various embodiments, determining whether the arc is an arc to be maintained or an arc to be extinguished includes determining that the arc is an arc to be extinguished based on a crest factor of the electrical treatment energy being greater than the threshold value.

In various embodiments, determining whether the arc is an arc to be maintained or an arc to be extinguished includes determining that the arc is an arc to be extinguished based on an amount of variation in crest factor of the electrical treatment energy over time being greater than the threshold value.

In various embodiments, determining that the arc is an arc to be extinguished includes determining voltage crest factor values over time based on a ratio of one of positive voltage peak or negative voltage peak of the electrical treatment energy over an RMS value of the electrical treatment energy, determining current crest factor values over time based on a ratio of one of positive current peak or negative current peak of the electrical treatment energy over an RMS value of the electrical treatment energy, high-pass filtering the voltage crest factor values to provide filtered voltage crest factor values, high-pass filtering the current crest factor values to provide filtered current crest factor values, combining absolute values of the filtered voltage crest factor values with absolute values of the filtered current crest factor values to provide combined crest factor values, low-pass filtering the combined crest factor values to provide resulting values indicative of an amount of variation in the voltage crest factor values and the current crest factor values, and determining that the arc is an arc to be extinguished when the resulting values exceed the threshold value for a time duration threshold.

In accordance with aspects of the present disclosure, the present disclosure includes an electrosurgical generator for controlling electrical treatment energy provided to an instrument. The generator includes one or more processors and at least one memory having instructions stored in the memory. The instructions, when executed by the one or more processors, cause the generator to provide electrical treatment energy to the instrument based on an indicated electrical energy level, access voltage signal values over time relating to voltage of the electrical treatment energy and/or current signal values over time relating to current of the electrical treatment energy, determine whether an arc generated by the instrument is an arc to be maintained or an arc to be extinguished based on a threshold value and at least one of: the voltage signal values or the current signal values, and control the electrical treatment energy based on determining that the arc is an arc to be extinguished.

In various embodiments, the instructions, when executed by the one or more processors, cause the generator, in determining whether the arc is an arc to be maintained or an arc to be extinguished, to determine that the arc is an arc to be extinguished based on a magnitude of change in peak-to-peak voltage of the electrical treatment energy over time being greater than the threshold value, wherein the threshold value changes corresponding to changes in the indicated electrical energy level.

In various embodiments, the instructions, when executed by the one or more processors, cause the generator, in determining whether the arc is an arc to be maintained or an arc to be extinguished, to determine that the arc is an arc to be extinguished based on a magnitude of change in peak-to-peak current of the electrical treatment energy over time being greater than the threshold value, wherein the threshold value changes corresponding to changes in the indicated electrical energy level.

In various embodiments, the instructions, when executed by the one or more processors, cause the generator, in determining whether the arc is an arc to be maintained or an arc to be extinguished, to determine that the arc is an arc to be extinguished based on a normalized change in peak-to-peak voltage of the electrical treatment energy over time being greater than the threshold value, wherein the normalized change in peak-to-peak voltage is a ratio of a magnitude of change in peak-to-peak voltage of the electrical treatment energy over one of: RMS voltage of the electrical treatment energy, RMS current of the electrical treatment energy, or average power of the electrical treatment energy. In this manner, the threshold value does not change for changes in the indicated electrical energy level.

In various embodiments, the instructions, when executed by the one or more processors, cause the generator, in determining whether the arc is an arc to be maintained or an arc to be extinguished, to determine that the arc is an arc to be extinguished based on a normalized change in peak-to-peak current of the electrical treatment energy over time being greater than the threshold value. The normalized change in peak-to-peak current is a ratio of a magnitude of change in peak-to-peak current of the electrical treatment energy over one of: RMS voltage of the electrical treatment energy, RMS current of the electrical treatment energy, or average power of the electrical treatment energy. In this manner, the threshold value does not change for changes in the indicated electrical energy level.

In various embodiments, the instructions, when executed by the one or more processors, cause the generator, in determining whether the arc is an arc to be maintained or an arc to be extinguished, to determine a peak-to-peak voltage at a first time as a difference between a positive voltage peak and a negative voltage peak of the electrical treatment energy at the first time, determine a peak-to-peak voltage at a second time as a difference between a positive voltage peak and a negative voltage peak of the electrical treatment energy at a second time, the second time being after the first time, determine a change in peak-to-peak voltage as an absolute value of a difference between the peak-to-peak voltage at the first time and the peak-to-peak voltage at the second time, determine an RMS voltage of the electrical treatment energy and an RMS current of the electrical treatment energy for the second time, determine a first normalized change in peak-to-peak voltage as a ratio of the change in peak-to-peak voltage over the RMS voltage, determine a second normalized change in peak-to-peak voltage as a ratio of the change in peak-to-peak voltage over the RMS current, access an impedance value indicative of an impedance of the arc, and determine that the arc is an arc to be extinguished when: the first normalized change in peak-to-peak voltage is greater than the threshold value and the impedance value is less than a first impedance threshold, or the second normalized change in peak-to-peak voltage is greater than a second threshold value and the impedance value is less than a second impedance threshold.

In various embodiments, the instructions, when executed by the one or more processors, cause the generator, in determining whether the arc is an arc to be maintained or an arc to be extinguished, to determine that the arc is an arc to be extinguished based on a crest factor of the electrical treatment energy being greater than the threshold value.

In various embodiments, the instructions, when executed by the one or more processors, cause the generator, in determining whether the arc is an arc to be maintained or an arc to be extinguished, to determine that the arc is an arc to be extinguished based on an amount of variation in crest factor of the electrical treatment energy over time being greater than the threshold value.

In various embodiments, the instructions, when executed by the one or more processors, cause the generator, in determining that the arc is an arc to be extinguished, to determine voltage crest factor values over time based on a ratio of one of positive voltage peak or negative voltage peak of the electrical treatment energy over an RMS value of the electrical treatment energy, determine current crest factor values over time based on a ratio of one of positive current peak or negative current peak of the electrical treatment energy over an RMS value of the electrical treatment energy, high-pass filter the voltage crest factor values to provide filtered voltage crest factor values, high-pass filter the current crest factor values to provide filtered current crest factor values, combine absolute values of the filtered voltage crest factor values with absolute values of the filtered current crest factor values to provide combined crest factor values, low-pass filter the combined crest factor values to provide resulting values indicative of an amount of variation in the voltage crest factor values and the current crest factor values, and determine that the arc is an arc to be extinguished when the resulting values exceed the threshold value for a time duration threshold.

In accordance with aspects of the present disclosure, the present disclosure includes an electrosurgical system. The system includes an instrument and an electrosurgical generator. The electrosurgical generator includes one or more processors and at least one memory having instructions stored in the memory. The instructions, when executed by the one or more processors, cause the generator to provide electrical treatment energy to the instrument based on an indicated electrical energy level, access voltage signal values over time relating to voltage of the electrical treatment energy and/or current signal values over time relating to current of the electrical treatment energy, determine whether an arc generated by the instrument is an arc to be maintained or an arc to be extinguished based on a threshold value and at least one of: the voltage signal values or the current signal values, and control the electrical treatment energy based on determining that the arc is an arc to be extinguished.

In accordance with aspects of the present disclosure, the present disclosure includes a method of controlling electrical treatment energy provided to an instrument. The method includes providing electrical treatment energy to the instrument based on an indicated electrical energy level, accessing voltage signal values over time relating to voltage of the electrical treatment energy or current signal values over time relating to current of the electrical treatment energy, accessing an impedance based on the current and voltage signal values, accessing a threshold value corresponding to the impedance, extracting voltage and current signals at three frequencies $f_{H1}$, $f_{H2}$, and $f_{H3}$, determining voltage-to-current phase signals $\varphi_{H1}$, $\varphi_{H2}$, and $\varphi_{H3}$ based on voltage and current signals at frequencies $f_{H1}$, $f_{H2}$, and $f_{H3}$, respectively, low-pass filtering the phase signals $\varphi_{H1}$, $\varphi_{H2}$, and $\varphi_{H3}$ to provide $\varphi_{H1\_filtered}$, $\varphi_{H2\_filtered}$, and $\varphi_{H3\_filtered}$, respectively, computing an arc detection trigger as: Trigger=$|\varphi_{H2\_filtered} - \varphi_{H1\_filtered}| + |\varphi_{H2\_filtered} - \varphi_{H3\_filtered}|$, determining that an arc is an arc to be extinguished if the Trigger value is greater than the threshold value, and controlling the electrical treatment energy based on determining that the arc is an arc to be extinguished.

In accordance with aspects of the present disclosure, the present disclosure includes a method of controlling electrical treatment energy provided to an instrument. The method includes providing electrical treatment energy to the instrument based on user settings, performing control feedback to achieve the user settings, accessing an absolute integrated error signal from the control feedback, determining that an arc is an arc to be extinguished based on the absolute integrated error being greater than a threshold value, and controlling the electrical treatment energy based on determining that the arc is an arc to be extinguished.

Further details and aspects of exemplary embodiments of the present disclosure are described in more detail below with reference to the appended figures.

BRIEF DESCRIPTION OF THE DRAWINGS

Various embodiments of the present disclosure are described with reference to the accompanying drawings wherein.

DETAILED DESCRIPTION

The present disclosure relates to electrosurgical systems and methods for controlling electrical treatment energy in connection with electrical arcs. As will be described herein in more detail, in one aspect of the present disclosure, when an electrosurgical generator provides electrical treatment energy to an instrument and determines that the instrument is creating an arc to be extinguished, the electrosurgical generator controls the electrical treatment energy based on that determination.

Where the term "approximately" is used herein in connection with a parameter having approximately a value, it is intended that the parameter can have exactly the value or can have another value which differs from the value due to environmental factors such as noise or due to hardware or software limitations such as, for example, number of bits, processor speed, or interrupt priority.

Figure 1:
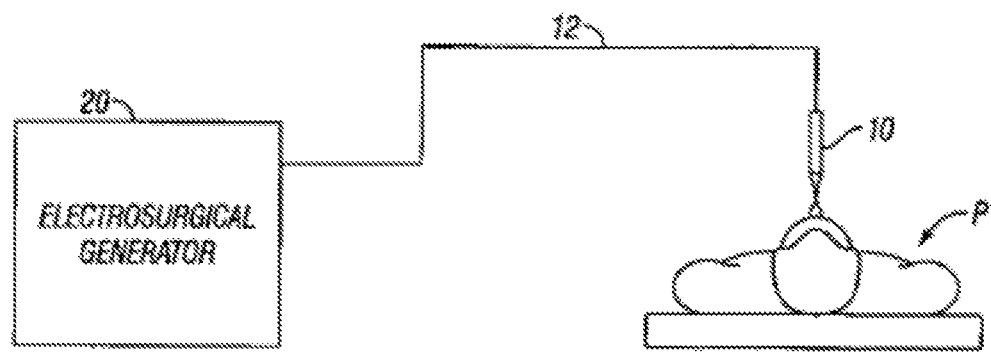
FIG. 1 is a diagram of an exemplary electrosurgical system, in accordance with aspects of the present disclosure.

Referring now to FIG. 1, there is shown a diagram of an exemplary electrosurgical system in accordance with aspects of the present disclosure. The system includes an electrosurgical instrument 10 having one or more electrodes for treating tissue of a patient P. The instrument 10 may be either a monopolar type including one or more active electrodes (e.g., electrosurgical cutting probe, fulguration electrode(s), etc.) or a bipolar type including one or more active and return electrodes (e.g., electrosurgical sealing forceps). Electrosurgical energy is supplied to the instrument 10 by a generator 20 via a supply line 12, allowing the instrument 10 to coagulate, seal, fulgurate, and/or otherwise treat tissue.

If the instrument 10 is a monopolar type instrument then energy may be returned to the generator 20 through a return electrode (not shown) which may be disposed on the patient's body. In addition, the generator 20 and the monopolar return electrode may be configured to monitor return electrode-to-patient contact to ensure that sufficient contact exists therebetween to mitigate chances of tissue damage. If the instrument 10 is a bipolar type instrument, the return electrode is disposed in proximity to the active electrode (e.g., on opposing jaws of a bipolar forceps).

The generator 20 includes input controls (e.g., buttons, activators, switches, touch screen, etc.) for controlling the generator 20. In addition, the generator 20 may include one or more display screens for providing the surgeon with a variety of output information (e.g., intensity settings, treatment complete indicators, etc.). The controls allow the surgeon to adjust power level of the electrical treatment energy and other parameters to achieve the desired treatment energy suitable for a particular procedure. It is also envisioned that the instrument 10 may include input controls which may be redundant with certain input controls of the generator 20. Placing the input controls at the instrument 10 allows for easier and faster modification of treatment energy parameters during the surgical procedure.

Figure 2:
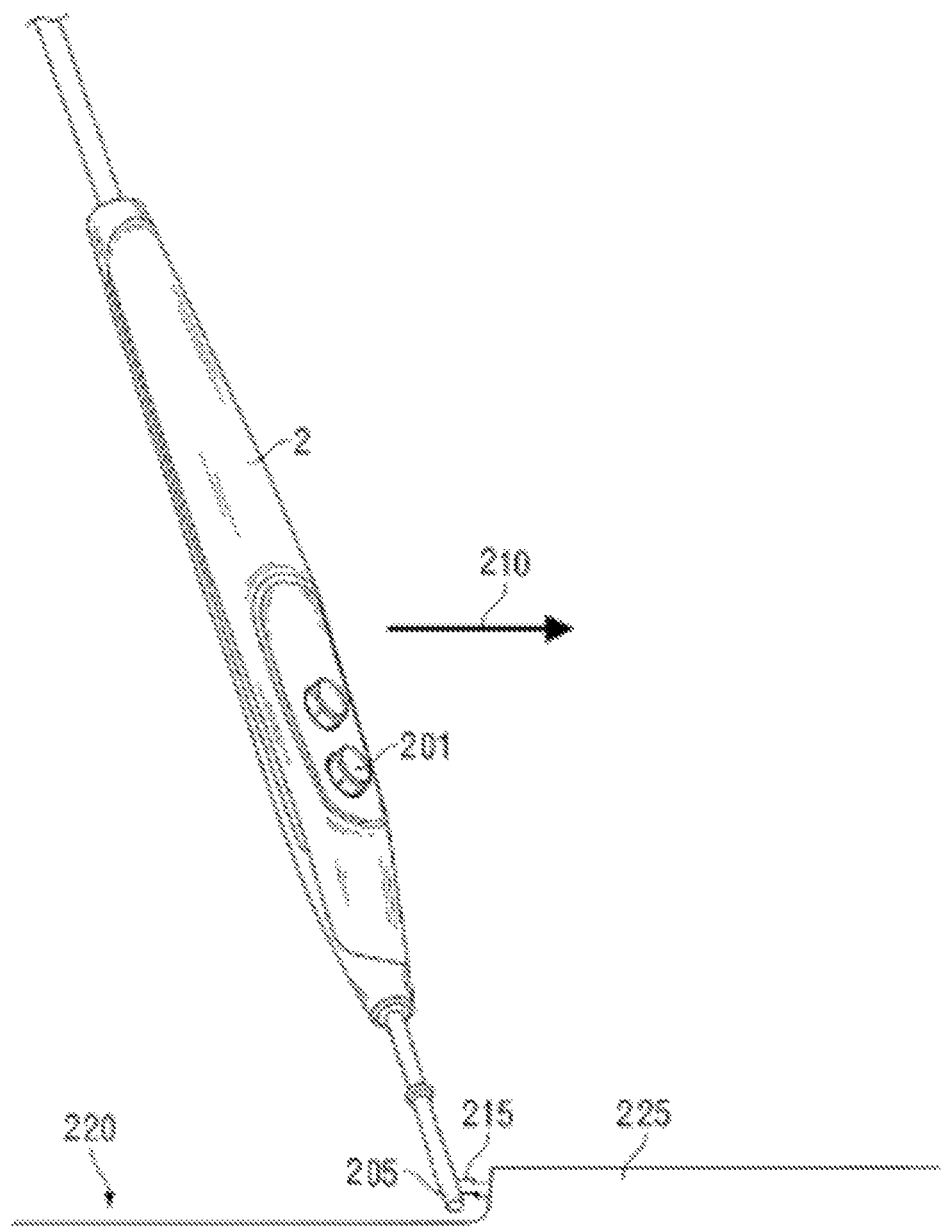
FIG. 2 is a diagram illustrating arcing during a procedure, in accordance with aspects of the present disclosure.

FIG. 2 is a diagram illustrating arcing during a monopolar procedure performed by the electrosurgical instrument 2. A surgeon sets the electrosurgical instrument 2 to a desired electrical treatment energy level via the user interface of the generator and activates the electrosurgical instrument 2 by depressing the activation switch 201, thus permitting electrosurgical treatment energy to be transmitted to the tip 205 of the instrument 2. The surgeon then commences the electrosurgical procedure by touching the tip 205 to the patient tissue.

In the illustrated example, arcing 215 to the tissue 225 occurs ahead of the tip 205 and can vaporize the tissue 225 before the probe 205 makes contact with the tissue 225. In various embodiments, arcs 215 form as the tip 205 approaches the tissue 225 and extinguish once the tissue within range has been vaporized (e.g., tissue site 220). If the movement of the tip 205 in the direction 210 is slow compared to the power level setting of the generator, then the arc 215 vaporizes the tissue 220 and extinguishes before the tip 205 moves close enough to other tissue 225 to reestablish an arc 215. If, on the other hand, the movement of the tip 205 is fast compared to the power level setting of the generator, then arcing may be reduced because of constant contact between the tip 205 and the tissue 225, or arcing may be maintained at a consistent level. Accordingly, different arcing situations may occur during an electrosurgical procedure. Additionally, various types of procedures other than tissue vaporization may involve arcing, such as tissue coagulation. Various ways of controlling an electrosurgical generator in arcing situations are disclosed in U.S. Pat. No. 7,651,492 and in U.S. Pat. No. 9,498,275. The entire contents of both of these U.S. patents are hereby incorporated by reference herein.

An electrosurgical generator in accordance with the present disclosure is enabled to detect arcs that should be extinguished, such as sustained arcs formed to metal, and to control the electrosurgical treatment energy in that situation. For example, various types of procedures may involve multiple instruments at the same surgical site, such as using forceps to grasp tissue and then using arcs from an electrosurgical probe to fulgurate the tissue grasped by the forceps. In this example, arcs may form to the forceps. If an electrosurgical generator is unable to determine that such an arc should be extinguished, the electrosurgical generator may operate to sustain the arc to metal and cause unintended harm to surrounding tissue. Accordingly, disclosed below are systems and methods for determining that an arc is an arc to be extinguished.

Figure 3:
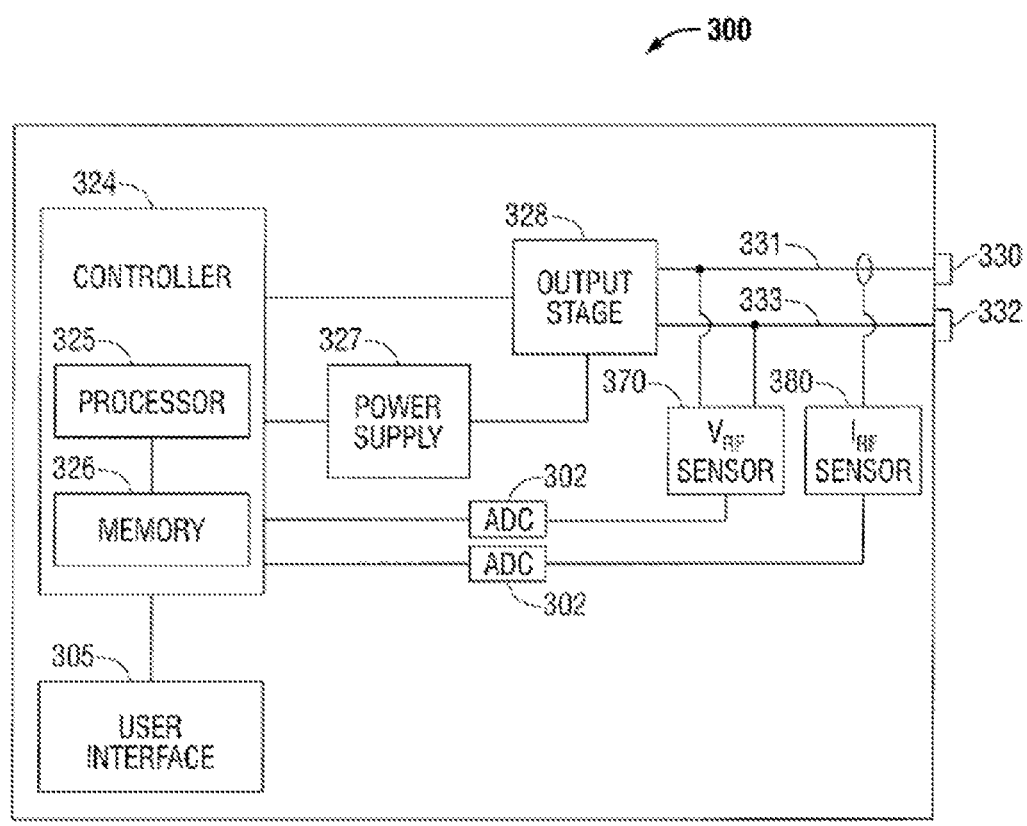
FIG. 3 is a block diagram of an exemplary electrosurgical generator, in accordance with aspects of the present disclosure.

FIG. 3 shows a schematic block diagram of one embodiment of a generator 300, which is configured to output electrosurgical energy, and generator components. The generator 300 includes a user interface 305, a controller 324, a power supply 327, and an output stage 328. The power supply 327 may be a direct current high voltage power supply and may be connected to an AC source (e.g., line voltage). The power supply 327 provides high voltage DC power to an output stage 328, which then converts high voltage DC power into electrosurgical alternating current and provides the electrosurgical energy to the active terminal 330. The alternating current is returned to the output stage 328 via the return terminal 332. The output stage 328 is configured to operate in a plurality of modes, during which the generator 300 outputs electrical treatment energy having specific power levels, peak voltages, crest factors, etc. In other embodiments, the generator 300 may be based on other types of suitable power supply or power conversion topologies.

The controller 324 includes a processor 325 (e.g., a microprocessor) operably connected to a memory 326, which may include transitory type memory (e.g., RAM) and/or non-transitory type memory (e.g., flash media and disk media). In various embodiments, the controller 324 may further include a field-programmable gate array (FPGA) for performing real-time analysis of the delivered current and/or voltage waveforms. The processor 325 includes an output port that is operably connected to the power supply 327 and/or output stage 328, allowing the processor 325 to control the output of the generator 300 according to either open- and/or closed-loop control schemes. Those skilled in the art will appreciate that the processor 325 may be substituted by any logic processor (e.g., control circuit) adapted to perform the calculations and/or set of instructions discussed herein.

In various embodiments, the generator 300 implements a closed-loop feedback control system, in which sensors measure a variety of tissue and generator output properties (e.g., impedance, output power, current and/or voltage, etc.), and provide feedback to the controller 324. The controller 324 then signals the power supply 327 and/or output stage 328, which then adjusts the DC power supply and/or output stage, respectively. The controller 324 also receives input signals from the user interface 305 of the generator 300. The controller 324 utilizes input signals received through the user interface 305 to adjust power outputted by the generator 300 and/or performs other control functions thereon. According to the present disclosure, an operator may input a desired power level setting via the user interface 305.

The generator 300 according to the present disclosure includes an RF current sensor 380 and an RF voltage sensor 370. The RF current sensor 380 is coupled to the active terminal 330 and provides measurements of the RF current supplied by the output stage 328. The RF voltage sensor 370 is coupled to the active and return terminals 330 and 332, and provides measurements of the RF voltage supplied by the output stage 328. In various embodiments, the RF voltage and current sensors 370 and 380 may be coupled to active lead 331 and return lead 333, which interconnect the active and return terminals 330 and 332 to the output stage 328, respectively.

The RF voltage and current sensors 370 and 380 provide the sensed RF voltage and current signals, respectively, to analog-to-digital converters (ADCs) 302. The ADCs 302 sample the sensed RF voltage and current signals and provide digital samples of the sensed RF voltage and current signals to the controller 324, which then may adjust the output of the power supply 327 and/or the output stage 328 in response to the digital samples of the sensed RF voltage and current signals. In various embodiments, the digital samples may be stored in the memory 326 until they are needed and may be deleted from the memory 326 when they are no longer needed.

In various embodiments, the controller 324 is adapted to determine various parameters based on the voltage and current signals values, including tissue impedance, crest factors, phase differences between the voltage and current signals, phase differences between certain frequency components of the voltage and current signals, peak voltage, peak current, RMS (root mean squared) voltage, RMS current, and average power, among other parameters. In various embodiments, one or more such parameters can be determined by separate hardware circuitry (not shown) rather than by the controller 324. Implementations of such parameter calculations by processor instructions and/or by hardware circuitry are known to persons skilled in the art. Usage of such parameters will be described below in connection with determining whether an arc is an arc to be maintained or an arc to be extinguished.

Figure 4:
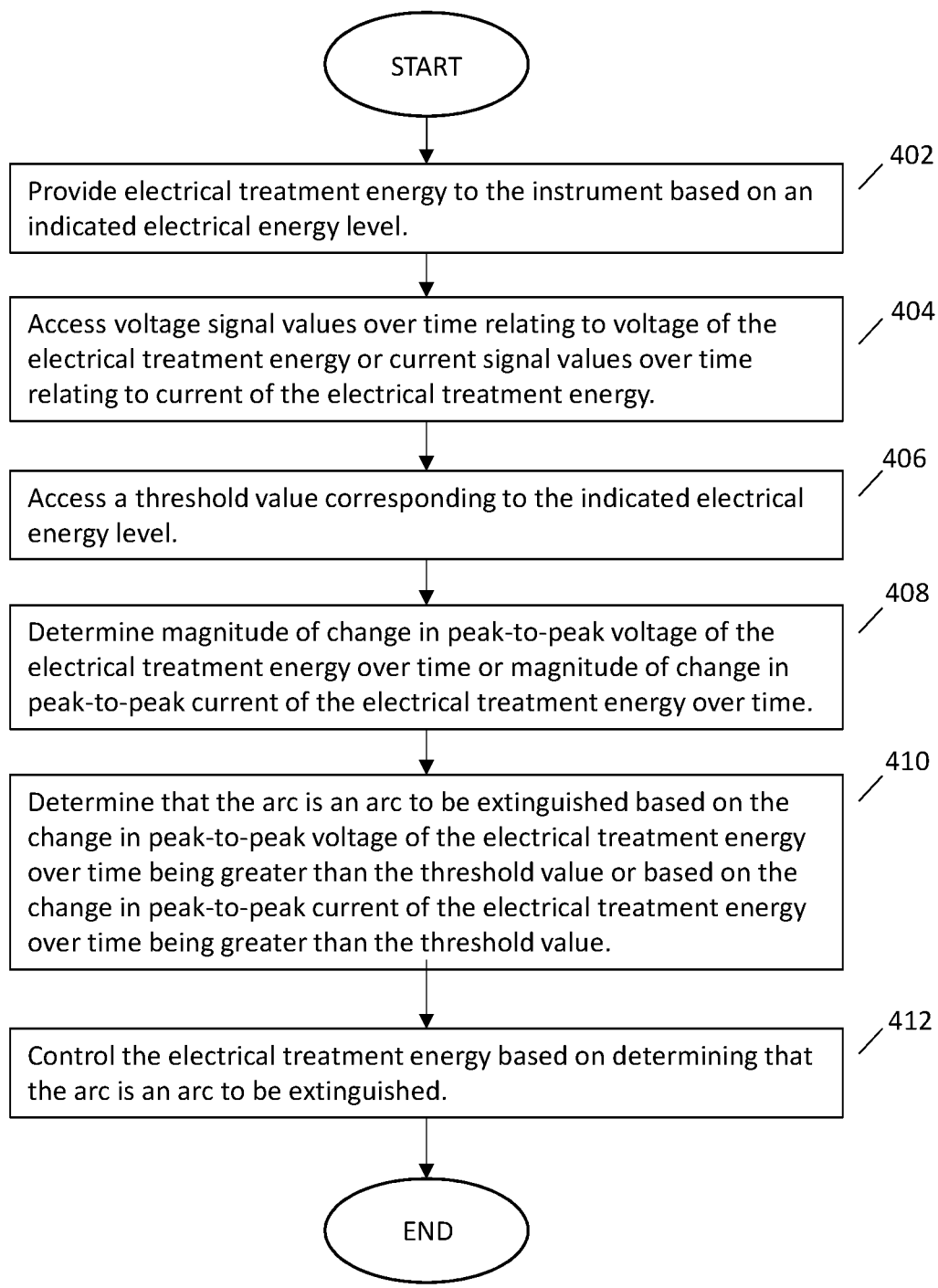
FIG. 4 is a flow diagram of an exemplary method of determining whether an arc is an arc to be maintained or an arc to be extinguished based on changes in peak-to-peak voltage or current over time, in accordance with aspects of the present disclosure.

Referring now to FIG. 4, there is shown a flow diagram of an exemplary method of determining whether an arc is an arc to be maintained or an arc to be extinguished based on changes in peak-to-peak voltage or current over time. It has been found that a sustained arc to metal results in larger changes in peak-to-peak voltage or current over time compared to changes in peak-to-peak voltage or current for an arc to tissue. The magnitude of change in peak-to-peak voltage or current over time can be compared to a threshold value to determine whether the arc is an arc to be maintained or an arc to be extinguished, such as a sustained arc to metal. However, the magnitude of change in the peak-to-peak voltage or current varies for different power setting levels. Accordingly, different threshold values are needed for different power setting levels.

At step 402, the generator provides electrical treatment energy to the instrument based on an electrical energy level indicated by the surgeon, which can be specified using the user interface (305, FIG. 3) of the generator. At step 404, the generator accesses voltage signal values over time relating to voltage of the electrical treatment energy or current signal values over time relating to current of the electrical treatment energy. As described above, such signal values can be digital samples stored in the memory (326, FIG. 3) of the controller. In various embodiments, the signal values need not be stored in the memory of a controller and can be stored in a buffer circuit. At step 406, the generator accesses a threshold value corresponding to the electrical energy level indicated by the surgeon. In various embodiments, a single threshold value can correspond to one or more electrical energy levels. The threshold values can be stored in and accessed from the memory of the controller.

At step 408, the generator determines, based on the signal values, a magnitude of change in peak-to-peak voltage of the electrical treatment energy over time or a magnitude of change in peak-to-peak current of the electrical treatment energy over time. As persons skilled in the art will understand, a magnitude is a positive value so that the magnitude of the change is a positive value regardless of the direction of change. In various embodiments, the generator includes a processor (325, FIG. 3) and the magnitude of change in peak-to-peak voltage or current can be determined at processor interrupts as the change in peak-to-peak voltage or current from one interrupt to the next interrupt. In various embodiments, the change in peak-to-peak voltage or current can be determined over another period of time. At step 410, if the magnitude of change in peak-to-peak voltage of the electrical treatment energy over time is greater than the threshold value, or if the magnitude of change in peak-to-peak current of the electrical treatment energy over time is greater than the threshold value, the generator determines that the arc is an arc to be extinguished. In various embodiments, the determination at step 410 considers the impedance of the arc, as determined from the voltage and current signal values. An example is described in connection with FIG. 6.

Then at step 412, the generator controls the electrical treatment energy based on determining that the arc is an arc to be extinguished. In various embodiments, the control at step 412 can include decreasing the electrical treatment energy for a predetermined time duration.

Figure 5:
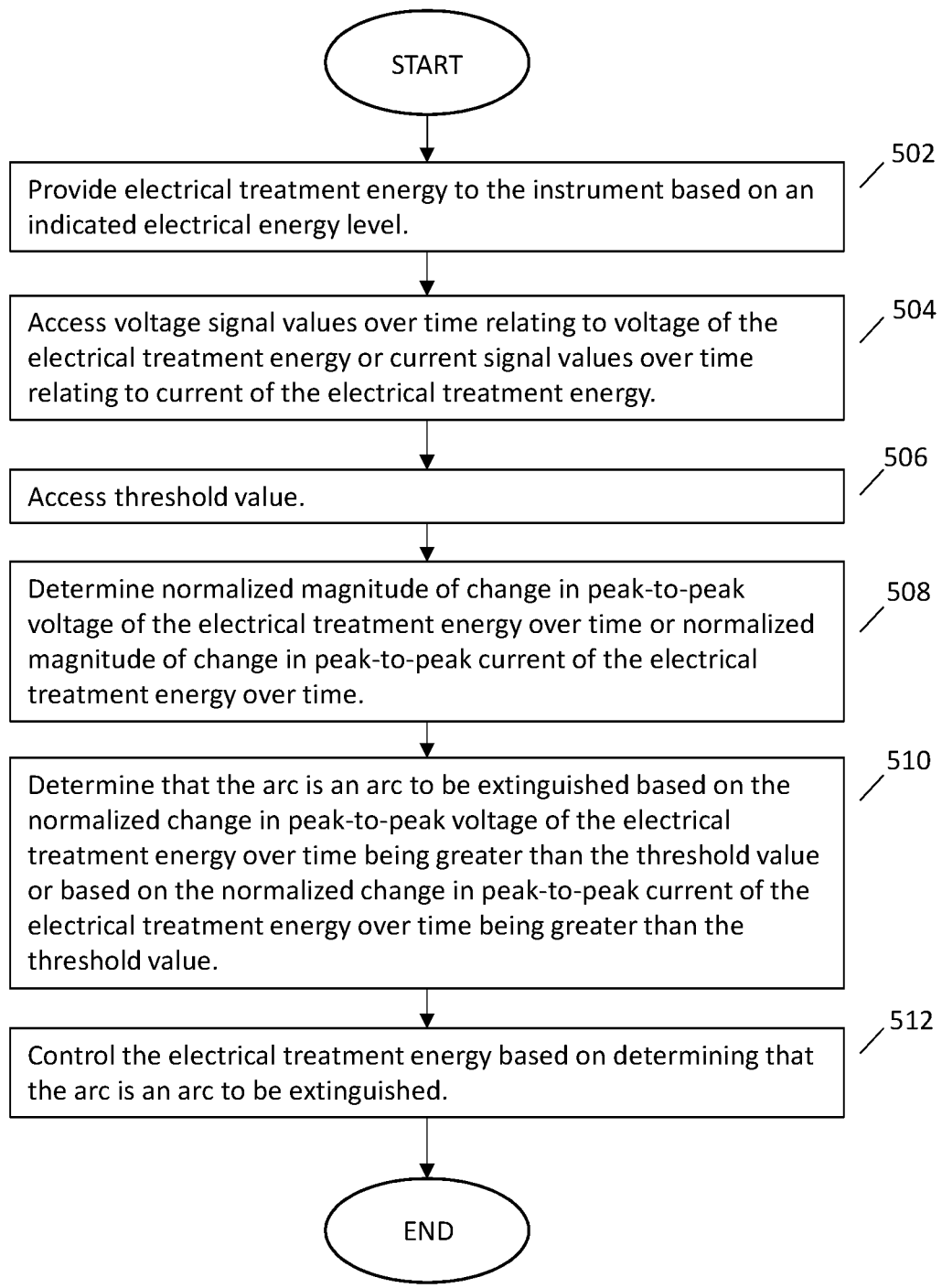
FIG. 5 is a flow diagram of an exemplary method of determining whether an arc is an arc to be maintained or an arc to be extinguished based on normalized changes in peak-to-peak voltage or current over time, in accordance with aspects of the present disclosure.

Referring now to FIG. 5, there is shown a flow diagram of an exemplary method of determining whether an arc is an arc to be maintained or an arc to be extinguished based on normalized changes in peak-to-peak voltage or current over time. The method of FIG. 5 is a variation of the method of FIG. 4 in which the magnitude of changes in peak-to-peak voltage or current is normalized so that the threshold value is not dependent on the power setting level. Accordingly, only one single threshold value is needed.

At step 502, the generator provides electrical treatment energy to the instrument based on an electrical energy level indicated by the surgeon, which can be specified using the user interface (305, FIG. 3) of the generator. At step 504, the generator accesses voltage signal values over time relating to voltage of the electrical treatment energy or current signal values over time relating to current of the electrical treatment energy. As described above, such signal values can be digital samples stored in the memory (326, FIG. 3) of the controller or signal values stored in a buffer circuit. At step 506, the generator accesses the threshold value. As mentioned above, there is a single threshold value regardless of the electrical energy level set by the surgeon. In various embodiments, the threshold value can be stored in and accessed from the memory of the controller. In various embodiments, the threshold value can be hard coded into a processor instruction.

At step 508, the generator determines, based on the signal values, a normalized magnitude of change in peak-to-peak voltage of the electrical treatment energy over time or a normalized magnitude of change in peak-to-peak current of the electrical treatment energy over time. The normalized magnitude of change is the magnitude of change divided by a quantity that scales with the electrical energy level. In various embodiments, the normalization parameter can be RMS voltage of the electrical treatment energy, RMS current of the electrical treatment energy, or average power of the electrical treatment energy. Accordingly, the normalized magnitude of change in peak-to-peak voltage would be the magnitude of change in peak-to-peak voltage divided by one of RMS voltage, RMS current, or average power. In the same way, the normalized magnitude of change in peak-to-peak current would be the magnitude of change in peak-to-peak current divided by one of RMS voltage, RMS current, or average power.

At step 510, if the normalized magnitude of change in peak-to-peak voltage of the electrical treatment energy over time is greater than the threshold value, or if the normalized magnitude of change in peak-to-peak current of the electrical treatment energy over time is greater than the threshold value, the generator determines that the arc is an arc to be extinguished. As discussed above in connection with FIG. 4, in various embodiments, the determination at step 510 considers the impedance of the arc, as determined from the voltage and current signal values. An example is described in connection with FIG. 6.

Then at step 512, the generator controls the electrical treatment energy based on determining that the arc is an arc to be extinguished. In various embodiments, the control at step 512 can include decreasing the electrical treatment energy for a predetermined time duration.

Figure 6:
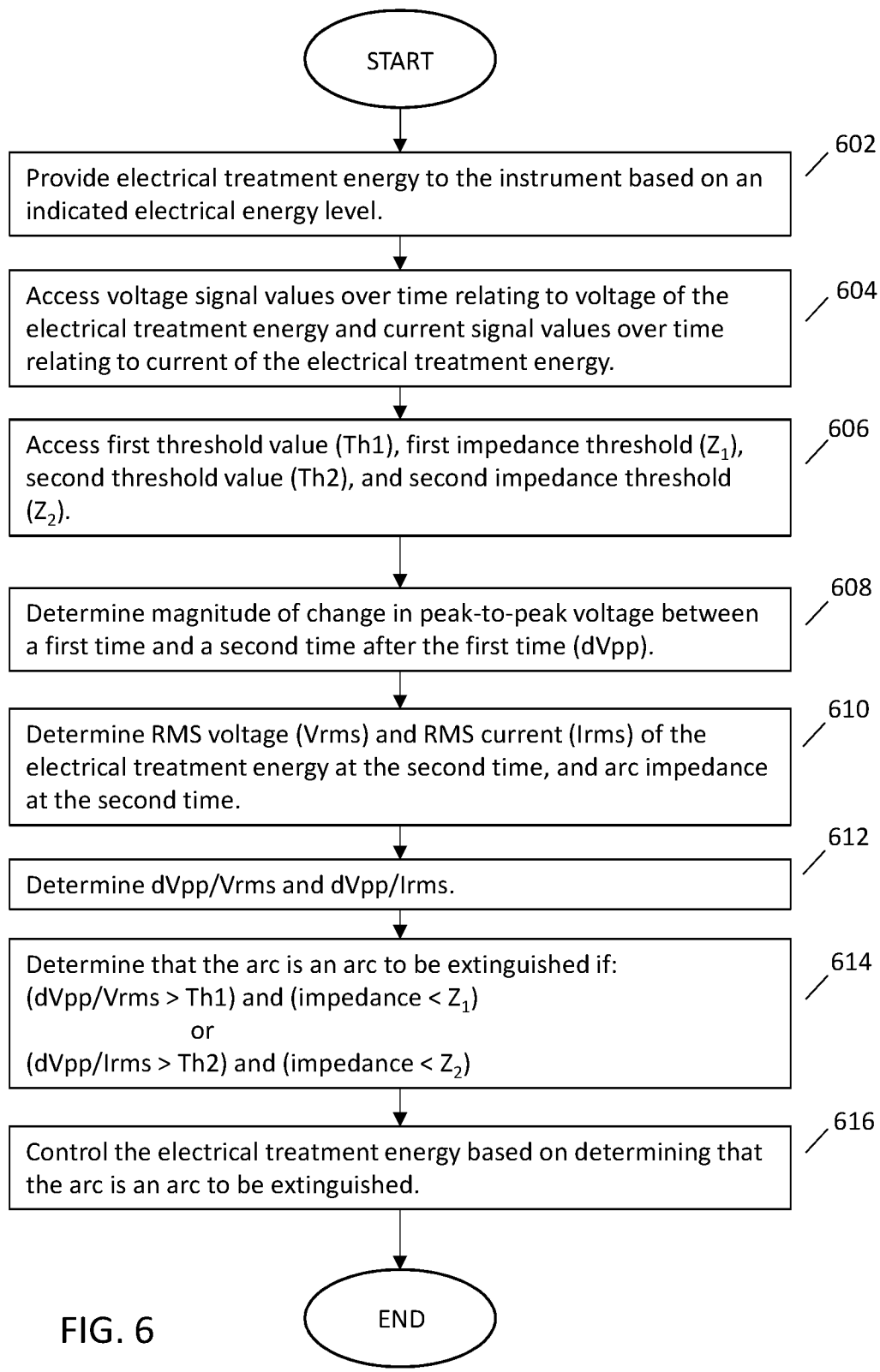
FIG. 6 is a flow diagram of an exemplary method of determining whether an arc is an arc to be maintained or an arc to be extinguished based on normalized changes in peak-to-peak voltage and impedance, in accordance with aspects of the present disclosure.

Referring now to FIG. 6, there is shown a flow chart of an exemplary method of determining whether an arc is an arc to be maintained or an arc to be extinguished based on normalized changes in peak-to-peak voltage over time and based on impedance.

At step 602, the generator provides electrical treatment energy to the instrument based on an electrical energy level indicated by the surgeon, which can be specified using the user interface (305, FIG. 3) of the generator. At step 604, the generator accesses voltage signal values over time relating to voltage of the electrical treatment energy or current signal values over time relating to current of the electrical treatment energy. As described above, such signal values can be digital samples stored in the memory (326, FIG. 3) of the controller or signal values stored in a buffer circuit. At step 606, the generator accesses four threshold values—a first threshold value (Th1), a first impedance threshold ($Z_1$), a second threshold value (Th2), and a second impedance threshold ($Z_2$). Based on normalization in the following steps, these threshold values do not depend on electrical treatment energy level and can be applied regardless of the electrical treatment energy level set by the surgeon. In various embodiments, the threshold values can be stored in and accessed from the memory of the controller. In various embodiments, the threshold value can be hard coded into processor instructions.

At step 608, the generator determines, based on the voltage signal values, the magnitude of change in peak-to-peak voltage between a first time and a second time after the first time (dVpp). At step 610, the generator determines, based on the voltage and current signal values, RMS voltage (Vrms) and RMS current (Irms) of the electrical treatment energy at the second time, and arc impedance at the second time. Then at step 612, the generator determines two normalized parameters—dVpp/Vrms and dVpp/Irms. In various embodiments, the parameter dVpp/Irms can be scaled.

At step 614, the generator determines that the arc is an arc to be extinguished if:

(dVpp/Vrms>Th1) and (impedance<$Z_1$)

or (dVpp/Irms>Th2) and (impedance<$Z_2$).

In various embodiments, $Z_1$ can be characterized as an impedance threshold that is used to determine whether to use Vrms or Irms to normalize the magnitude of change in peak-to-peak voltage dVpp, and $Z_2$ can be described as an impedance threshold above which the generator will not intentionally extinguish an arc. In various embodiments, $Z_1$ is 1350 ohms and $Z_2$ is 3000 ohms. In various embodiments, the impedance thresholds can have other values. In various embodiments, the values of $Z_1$ and $Z_2$ can be derived from analyzing voltage and current data relating to arcs.

Then at step 616, the generator controls the electrical treatment energy based on determining that the arc is an arc to be extinguished. In various embodiments, the control at step 616 can include decreasing the electrical treatment energy for a predetermined time duration. In various embodiments, the control at step 616 can include decreasing the electrical treatment energy for a time duration that is computed or that is based on sensed electrical data, such as voltage, current, and/or impedance data. For example, the electrical treatment energy can be decreased until the impedance rises and indicates an open circuit condition, such as an impedance greater than 7,000 ohms. In various embodiments, the control at step 616 can include turning off the energy delivery for a predetermined or computed time duration, or for a time duration that is based on sensed electrical data.

Accordingly, described above in connection with FIGS. 4-6 are methods for determining whether an arc is an arc to be maintained or an arc to be extinguished based on magnitude of changes in peak-to-peak voltage or current. The determinations can be performed by a processor executing instructions, and can be performed as instructions executed during processor interrupts. In various embodiments, the determinations can be performed approximately every 0.5 milliseconds. In various embodiments, the threshold values of FIGS. 4-6 can be obtained by analyzing empirical data corresponding to arcs to tissue and empirical data corresponding to arcs to non-tissue, such as metal. The empirical data will reveal the boundaries between parameter values corresponding to an arc to be maintained and the parameter values corresponding to an arc to be extinguished, such as a sustained arc to metal. Because different generators will be implemented differently, the threshold values may be dependent on the particular model or brand of the generator. In light of the methods disclosed herein, obtaining empirical data and determining the threshold values for different generators are within the abilities and competencies of persons skilled in the art. This manner of determining threshold values also applies to FIGS. 7-12 below.

The following will now describe a method of determining whether an arc is an arc to be maintained or an arc to be extinguished based on crest factors. As used herein, and as understood in the art, crest factor refers to a ratio of a peak value over an RMS value. In various embodiments, the peak value can be a positive peak voltage, a negative peak voltage, a positive peak current, or a negative peak current. In various embodiments, the RMS value can be RMS voltage (Vrms) or RMS current (Irms). Various combinations of these peak values and RMS values are all contemplated to be crest factors. With reference also to FIG. 3, in various embodiments, a crest factor value can be determined by the controller 324 based on the current signals and the voltage signals sensed by the current and voltage sensors 370, 380.

Figure 7:
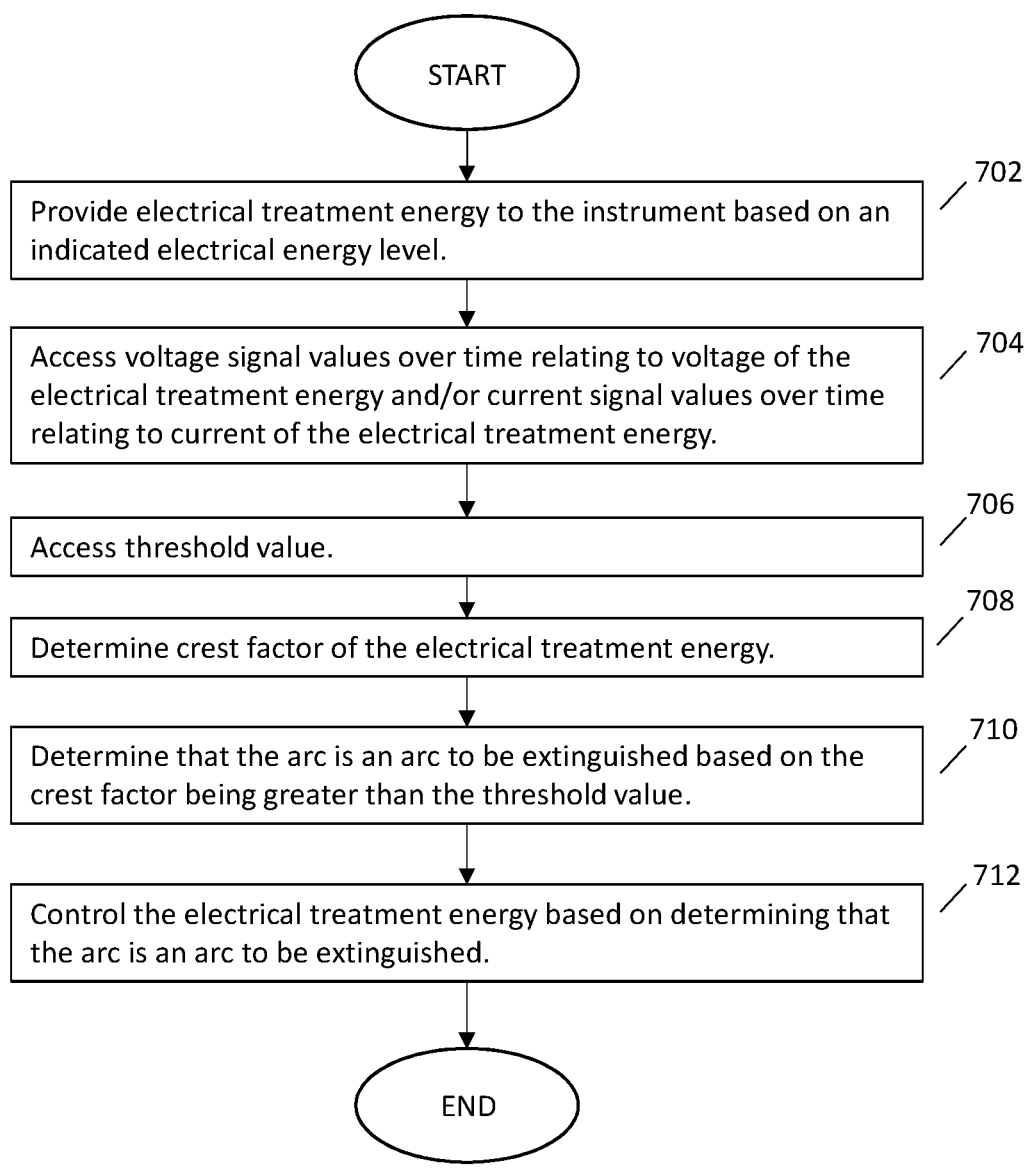
FIG. 7 is a flow diagram of an exemplary method of determining whether an arc is an arc to be maintained or an arc to be extinguished based on crest factor, in accordance with aspects of the present disclosure.

Referring now to FIG. 7, there is shown a flow diagram of an exemplary method of determining whether an arc is an arc to be maintained or an arc to be extinguished based on crest factor. It has been found that a sustained arc to non-tissue, such as an arc to metal, results in larger crest factor compared to a crest factor for an arc to tissue. In various embodiments, the crest factor value can be compared to a threshold value to determine whether the arc is an arc that should be maintained or an arc that should be extinguished, such as an arc to metal. Because a crest factor is defined by an RMS value, which scales with different power setting levels, crest factor inherently does not depend on the power setting level. Accordingly, the same threshold value can be applied to different power setting levels.

At step 702, the generator provides electrical treatment energy to the instrument based on an electrical energy level indicated by the surgeon, which can be specified using the user interface (305, FIG. 3) of the generator. At step 704, the generator accesses voltage signal values over time relating to voltage of the electrical treatment energy or current signal values over time relating to current of the electrical treatment energy. As described above, such signal values can be digital samples stored in the memory (326, FIG. 3) of the controller or signal values stored in a buffer circuit. At step 706, the generator accesses the threshold value. As mentioned above, there is a single threshold value regardless of the electrical energy level set by the surgeon. In various embodiments, the threshold value can be stored in and accessed from the memory of the controller. In various embodiments, the threshold value can be hard coded into a processor instruction.

At step 708, the generator determines a crest factor value based on the signal values. As mentioned above, the crest factor can be based on a peak value that is one of a positive peak voltage, a negative peak voltage, a positive peak current, or a negative peak current, and can be based on an RMS value that is one of RMS voltage (Vrms) or RMS current (Irms). At step 710, if the crest factor value is greater than the threshold value, the generator determines that the arc is an arc to be extinguished. In various embodiments, step 710 can consider impedance in making the determination.

Then at step 712, the generator controls the electrical treatment energy based on determining that the arc is an arc to be extinguished. In various embodiments, the control at step 712 can include decreasing the electrical treatment energy for a predetermined time duration.

Figure 8:
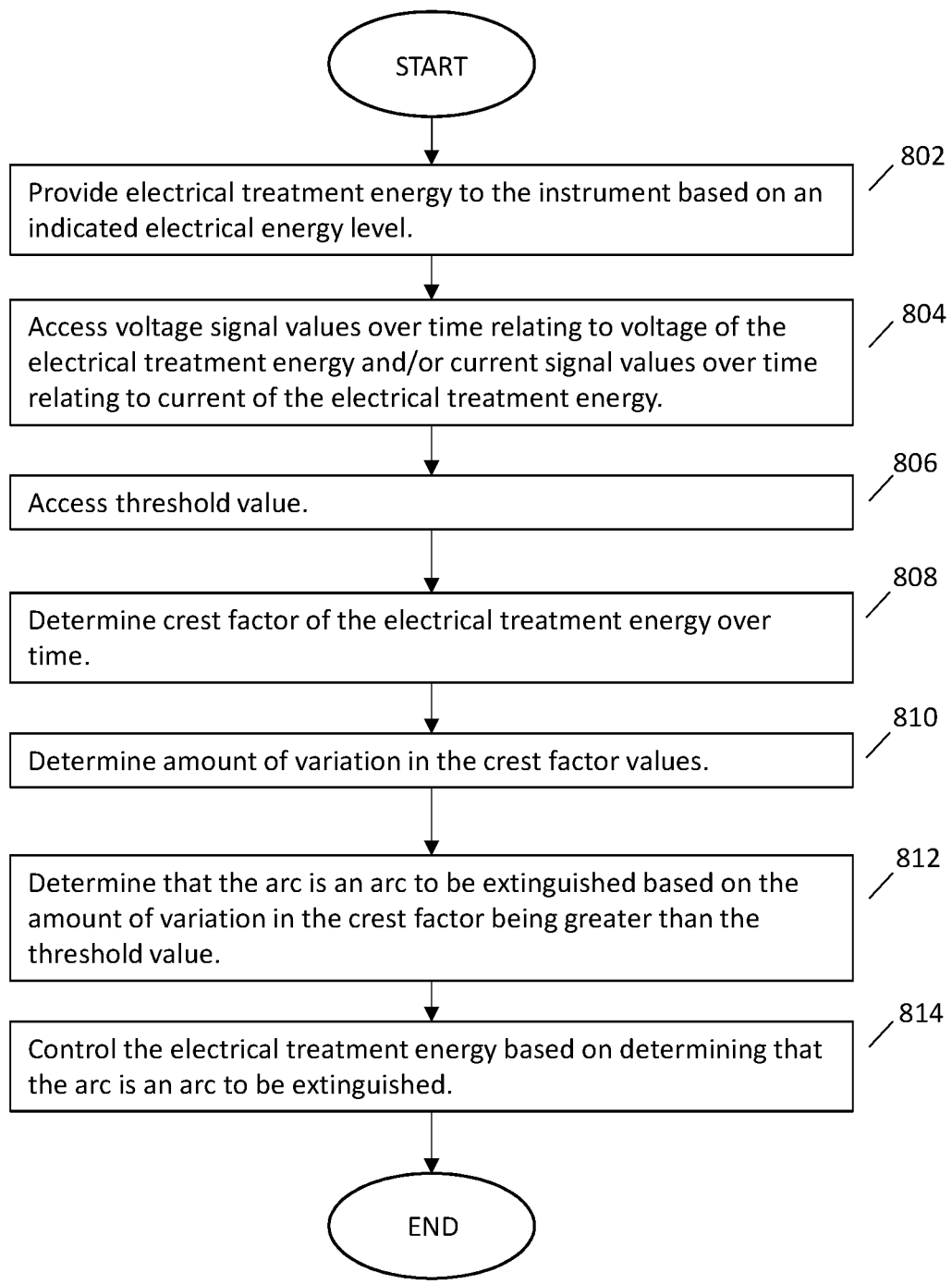
FIG. 8 is a flow diagram of an exemplary method of determining whether an arc is an arc to be maintained or an arc to be extinguished based on an amount of variation in crest factor over time, in accordance with aspects of the present disclosure.

Referring now to FIG. 8, there is shown a flow diagram of an exemplary method of determining whether an arc is an arc to be maintained or an arc to be extinguished based on an amount of variation in crest factor over time. It has been found that a sustained arc to non-tissue, such as an arc to metal, results in larger variations in crest factor over time compared to variations in crest factor for an arc to tissue. The amount of variation in crest factor value can be compared to a threshold value to determine whether the arc is an arc to be maintained or an arc to be extinguished. Because amount of variation is a metric that does not depend on the power setting level, the same threshold value can be applied to different power setting levels.

At step 802, the generator provides electrical treatment energy to the instrument based on an electrical energy level indicated by the surgeon, which can be specified using the user interface (305, FIG. 3) of the generator. At step 804, the generator accesses voltage signal values over time relating to voltage of the electrical treatment energy or current signal values over time relating to current of the electrical treatment energy. As described above, such signal values can be digital samples stored in the memory (326, FIG. 3) of the controller or signal values stored in a buffer circuit. At step 806, the generator accesses the threshold value. As mentioned above, there is a single threshold value regardless of the electrical energy level set by the surgeon. In various embodiments, the threshold value can be stored in and accessed from the memory of the controller. In various embodiments, the threshold value can be hard coded into a processor instruction.

At step 808, the generator determines crest factor values over time based on the signal values. As mentioned above, the crest factor can be based on a peak value that is one of a positive peak voltage, a negative peak voltage, a positive peak current, or a negative peak current, and can be based on an RMS value that is one of RMS voltage (Vrms) or RMS current (Irms). At step 810, the generator determines the amount of variation in the crest factor values. There are various ways contemplated for determining amount of variation. For example, without limitation, an amount of variation can be determined using statistical measures, such as standard deviation. Another way to determine amount of variation is by use of filters, as explained in connection with FIG. 9. Other ways of determining amount of variation are contemplated to be within the scope of the present disclosure.

At step 812, if the amount of variation in crest factor is greater than the threshold value, the generator determines that the arc is an arc to be extinguished. Then at step 814, the generator controls the electrical treatment energy based on determining that the arc is an arc to be extinguished. In various embodiments, the control at step 814 can include decreasing the electrical treatment energy for a predetermined time duration.

Figure 9:
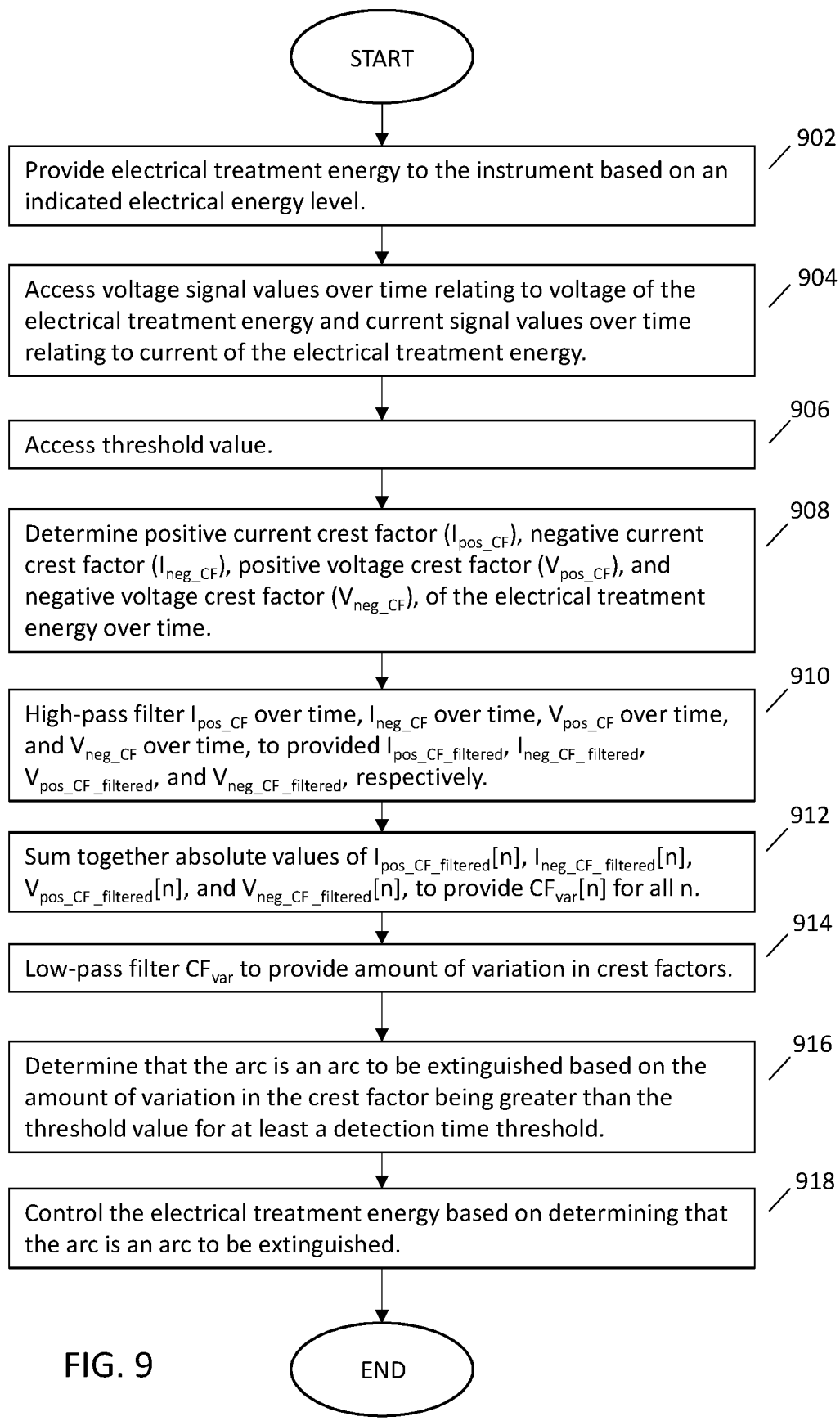
FIG. 9 is a flow chart of one particular embodiment of the method of FIG. 8, in accordance with aspects of the present disclosure.

FIG. 9 shows a flow chart of one particular embodiment of the method of FIG. 8, for determining an amount of variation in crest factor values over time. In particular, FIG. 9 shows one way to determine amount of variation using high-pass and low-pass filters.

At step 902, the generator provides electrical treatment energy to the instrument based on an electrical energy level indicated by the surgeon, which can be specified using the user interface (305, FIG. 3) of the generator. At step 904, the generator accesses voltage signal values over time relating to voltage of the electrical treatment energy and current signal values over time relating to current of the electrical treatment energy. As described above, such signal values can be digital samples stored in the memory (326, FIG. 3) of the controller or signal values stored in a buffer circuit. At step 906, the generator accesses the threshold value. As mentioned above, there is a single threshold value regardless of the electrical energy level set by the surgeon. In various embodiments, the threshold value can be stored in and accessed from the memory of the controller. In various embodiments, the threshold value can be hard coded into a processor instruction.

At step 908, the generator determines crest factor values over time based on the signal values, including positive current crest factor ($I_{pos\_CF}$) based on positive peak current, negative current crest factor ($I_{neg\_CF}$) based on negative peak current, positive voltage crest factor ($V_{pos\_CF}$) based on positive peak voltage, and negative voltage crest factor ($V_{neg\_CF}$) based on negative peak voltage, of the electrical treatment energy over time. At step 910, the generator high-pass filters $I_{pos\_CF}$ over time to provide $I_{pos\_CF\_filtered}$, high-pass filters $I_{neg\_CF}$ over time to provide $I_{neg\_CF\_filtered}$, high-pass filters $V_{pos\_CF}$ over time to provide $V_{pos\_CF\_filtered}$, and high-pass filters $V_{neg\_CF}$ over time to provided $V_{neg\_CF\_filtered}$. The high-pass filtering removes a DC component from the crest factors so that the filtered crest factor values represent the crest factor variations centered at zero. Thus, the high-pass filtering passes the changes so that the result is a zero-centered pattern of pulses which represent each change in crest factor. In various embodiments, the high pass filter can be a digital first order, recursive filter with a cut-off frequency around 500 kHz.

At step 912, the absolute values of the four filtered crest factors are added together. In particular, each of the filtered crest factors have multiple values, such as N values, e.g., $I_{pos\_CF\_filtered}[n]$, $I_{neg\_CF\_filtered}[n]$, $V_{pos\_CF\_filtered}[n]$, and $V_{neg\_CF\_filtered}[n]$, for n=1 . . . N. For each n, the generator determines combined crest factor values:

$$CF_{var}[n]=|I_{pos\_CF\_filtered}[n]|+|I_{neg\_CF\_filtered}[n]|+ |V_{pos\_CF\_filtered}[n]|+|V_{neg\_CF\_filtered}[n]|.$$

In this way, the variations from each of the filtered crest factors are combined, and the resulting values $CF_{var}$ capture the variations among the four crest factors.

At step 914, the values $CF_{var}$ are low-pass filtered. Because $CF_{var}$ is as sum of absolute values, all values of $CF_{var}$ are positive. Accordingly, the $CF_{var}$ sequence will have a DC component, and low-pass filtering the $CF_{var}$ sequence provides the DC component. This DC component of $CF_{var}$ represents the amount of variation in the crest factors. In various embodiments, design of the low-pass filter involves a balancing of false-positive detection and detection time. For example, a longer detection time leads to fewer false-positives in determining that an arc should be extinguished, whereas a shorter detection time leads to more false-positives in determining that an arc should be extinguished. In various embodiments, in balancing these factors, the low-pass filter is a digital second order, recursive filter having 5 milliseconds to 99% rise time.

At step 916, if the amount of variation in crest factors is greater than the threshold value for at least a detection time threshold, the generator determines that the arc is an arc to be extinguished. In various embodiments, the threshold value is 0.15 and the detection time threshold is 15 milliseconds. Then at step 918, the generator controls the electrical treatment energy based on determining that the arc is an arc to be extinguished. The control in step 918 is described in more detail below with respect to FIG. 10. In various embodiments, the determination at step 916 considers the impedance of the arc, as determined from the voltage and current signal values. In various embodiments, at step 916, the generator does not determine that the arc is an arc to be extinguished if the arc impedance is greater than 15,000 ohms.

Although the embodiment of FIG. 9 involves using four crest factors, in various embodiments, less than four crest factors can be used. In various embodiments, the operation of FIG. 9 uses only a single current crest factor and a single voltage crest factor. In various embodiments, the single current crest factor can be the larger of the positive current crest factor and the negative current crest factor. In various embodiments, the single voltage crest factor can be the larger of the positive voltage crest factor and the negative voltage crest factor.

Figure 10:
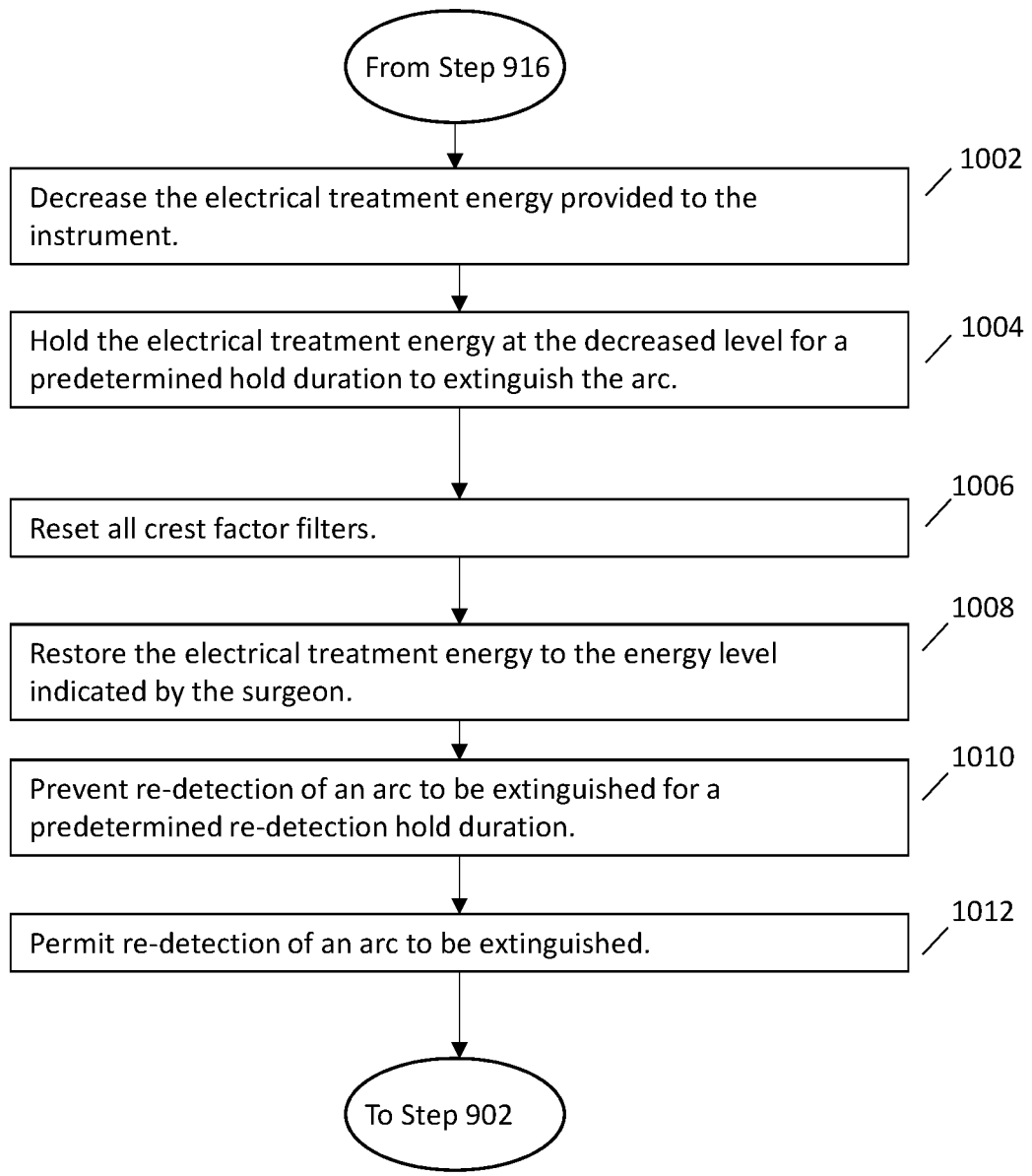
FIG. 10 is a flow chart of one embodiment of controlling electrical treatment energy when it is determined in the method of FIG. 9 that an arc is an arc to be extinguished, in accordance with aspects of the present disclosure.

Referring now to FIG. 10, there is shown a flow chart of one embodiment of controlling electrical treatment energy when it is determined in the method of FIG. 9 that an arc is an arc to be extinguished. The illustrated embodiment is exemplary and non-limiting, and other ways are contemplated for controlling electrical treatment energy when there is an arc to be extinguished.

At step 1002, when it is determined that an arc is an arc to be extinguished, the generator decreases the electrical treatment energy provided to the instrument. In various embodiments, the electrical treatment energy is deceased to a low energy level, such as 5 Watts. In various embodiments, the low energy level can be another level, such a zero watts. In various embodiments, the low energy level can be a percentage of the power level set by the surgeon, such as 10% of the indicated power level, or another percentage. In step 1004, the generator holds the electrical treatment energy at the decreased level for a predetermined hold duration to extinguish the arc. In various embodiments, the predetermined hold duration can be 25 milliseconds, 60 milliseconds, or another duration.

At step 1006, the generator resets all crest factor filters, and at step 1008, the generator restores the electrical treatment energy to the energy level indicated by the surgeon. At step 1010, the generator prevents re-detection of an arc to be extinguished for a predetermined re-detection hold duration. In one embodiment, the re-detection hold duration is 5 milliseconds. Then at step 1012, after the re-detection hold duration elapses, the generator permits re-detection of an arc to be extinguished.

Accordingly, described above in connection with FIGS. 7-10 are systems and methods for determining whether an arc is an arc to be maintained or an arc to be extinguished based on crest factors. The determinations can be performed by a processor executing instructions, and can be performed as instructions executed during processor interrupts. In various embodiments, the determinations can be performed approximately every 0.44 milliseconds, every 15 milliseconds, or at another time interval. Comparing the crest factor methodology of FIG. 10 to the change in peak-to-peak methodology of FIGS. 4-6, the crest factor methodology is meaningfully slower. This slower operation of the crest factor methodology of FIG. 10 depends in large part on the amount of time required for the high-pass and low-pass filters to operate. Whereas the crest factor methodology of FIG. 10 requires filters, the change in peak-to-peak methodology of FIGS. 4-6 does not require any filtering.

In various embodiments, the threshold values and hold durations of FIGS. 7-10 can be obtained by analyzing empirical data corresponding to arcs to tissue and empirical data corresponding to arcs to metal. The empirical data will reveal the boundaries between parameter values corresponding to an arc to be maintained and the parameter values corresponding to an arc to be extinguished. Because different generators will be implemented differently, the threshold values may be dependent on the particular model or brand of the generator. In light of the methods disclosed herein, obtaining empirical data and determining the threshold values and hold durations for different generators are within the abilities and competencies of persons skilled in the art.

Figure 11:
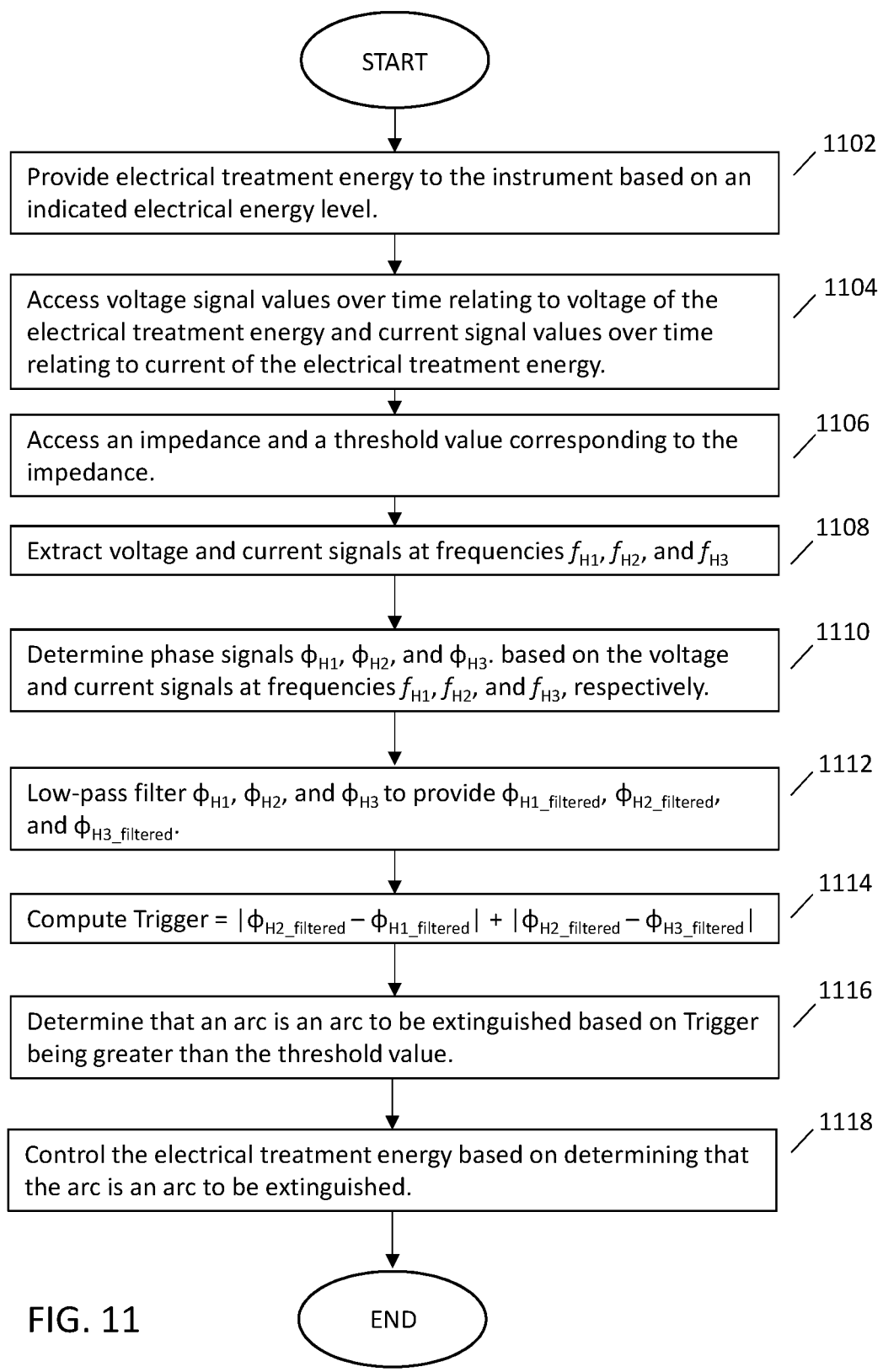
FIG. 11 is a flow chart of a method of determining whether an arc is an arc to be extinguished based on phase differences between current and voltage of the electric treatment energy at particular frequencies, in accordance with aspects of the present disclosure.
Figure 12:
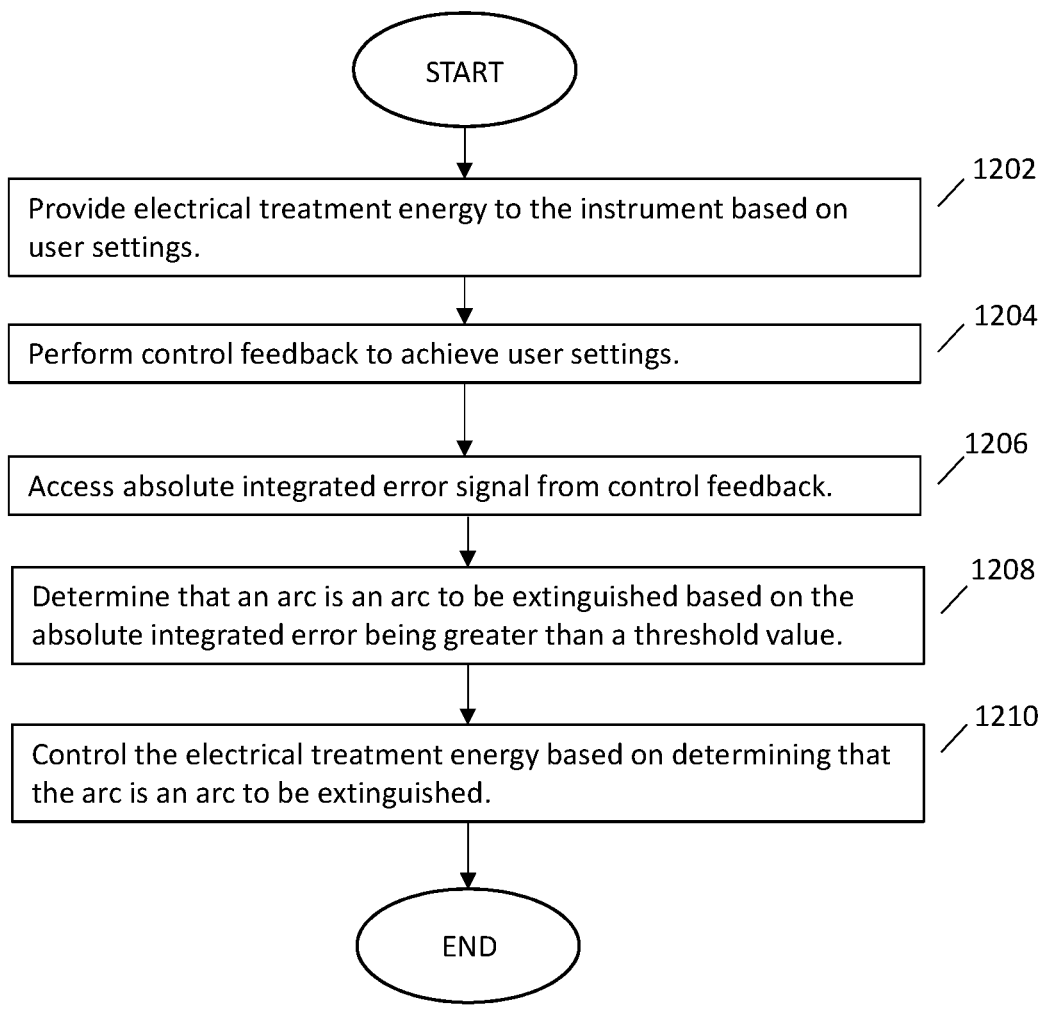
FIG. 12 is a flow chart of a method of determining whether an arc is an arc to be extinguished based on a feedback control parameter, in accordance with aspects of the present disclosure.

The follow description with respect to FIGS. 11 and 12 describe methods of determining whether an arc is an arc to be maintained or an arc to be extinguished, such as a sustained arc to metal.

FIG. 11 is a flow chart of a method of determining that an arc is an arc that should be extinguished based on phase differences between current and voltage of the electric treatment energy at particular frequencies. With reference to FIG. 3, the particular frequencies include the fundamental frequency of the electrical treatment energy waveform output by the output stage 328, which will be denoted as $f_{H1}$. The other frequencies relate to the output stage 328. As described above, the power supply 327 provides high voltage DC power to an output stage 328, which then converts high voltage DC power into electrosurgical alternating current. Accordingly, the output stage 328 includes a resonant inverter. In various embodiments, the particular frequencies include a first resonant frequency $f_{H2}$ of the inverter circuit when there is no load (i.e., open circuit), and a second resonant frequency $f_{H3}$ of the inverter circuit when there is a short circuit load.

It has been found that during an arc that should be extinguished, such as a sustained arc to metal, certain phase information for the three frequencies $f_{H1}$, $f_{H2}$, and $f_{H3}$, correlate to such an arc. In particular, the voltage to current phase difference at frequency $f_{H1}$ will be denoted as $\varphi_{H1}$, the voltage to current phase difference at frequency $f_{H2}$ will be denoted as $\varphi_{H2}$, and the voltage to current phase difference at frequency $f_{H3}$ will be denoted as $\varphi_{H3}$. It has been found, also, that the threshold value for arc differentiation in accordance with this methodology varies depending on the impedance determined from the current and voltage signals, which relates to the matched load of the inverter circuit (the load the inverter develops at its highest, most efficient power output). Accordingly, there are multiple threshold values corresponding to different impedance values.

At step 1102, the generator provides electrical treatment energy to the instrument based on an electrical energy level indicated by the surgeon, which can be specified using the user interface (305, FIG. 3) of the generator. At step 1104, the generator accesses voltage signal values over time relating to voltage of the electrical treatment energy or current signal values over time relating to current of the electrical treatment energy. As described above, such signal values can be digital samples stored in the memory (326, FIG. 3) of the controller or signal values stored in a buffer circuit. At step 1106, the generator accesses or determines an impedance based on the current and voltage signal values, and accesses a threshold value corresponding to the impedance. In various embodiments, the threshold values can be stored in and accessed from the memory of the controller.

At step 1108, the generator extracts voltage and current signals at frequencies $f_{H1}$, $f_{H2}$, and $f_{H3}$. At step 1110, the generator determines voltage-to-current phase signals $\varphi_{H1}$, $\varphi_{H2}$, and $\varphi_{H3}$, based on the voltage and current signals at frequencies $f_{H1}$, $f_{H2}$, and $f_{H3}$, respectively. In various embodiments, the operations of steps 1108 and 1110 can be performed based on Goertzel filters, Discrete Fourier Transforms (DFT), Fast Fourier Transforms (FFT), or narrowband filters. At step 1112, the generator low-pass filters the phase signals $\varphi_{H1}$, $\varphi_{H2}$, and $\varphi_{H3}$ to provide $\varphi_{H1\_filtered}$, $\varphi_{H2\_filtered}$, and $\varphi_{H3\_filtered}$, respectively. At step 1114, the arc detection trigger value is computed as:

$$\text{Trigger} = |\varphi_{H2\_filtered} - \varphi_{H1\_filtered} - \varphi_{H1\_filtered}| + |\varphi_{H2\_filtered} - \varphi_{H3\_filtered}|.$$

In various embodiments, the trigger can be described as the magnitude of the change in phase between components H2 and H3 in relation to the fundamental drive frequency component H1. At step 1116, the generator determines that an arc is an arc to be extinguished if the Trigger value is greater than the threshold value.

And at step 1118, the generator controls the electrical treatment energy based on determining that an arc is an arc to be extinguished. In various embodiments, the generator can perform a control procedure similar to that shown in FIG. 10, including decreasing the electrical treatment energy for a predetermined hold duration to extinguish the arc, resetting all filters, restoring the electrical treatment energy to the energy level indicated by the surgeon, preventing re-detection of the arc for a predetermined re-detection hold duration, and then permitting re-detection of an arc after the re-detection hold duration elapses.

Referring now to FIG. 12, there is shown a method of determining that an arc should be extinguished based on a feedback control parameter referred to herein as absolute integrated error. Referring also to FIG. 3, the generator 300 implements a closed-loop feedback control system, in which sensors provide feedback to the controller 324. The controller 324 then signals the power supply 327 and/or output stage 328, which then adjusts the DC power supply and/or output stage, respectively. In the feedback operation, an error between an intended parameter value and the actual parameter value is tracked over time by computing the absolute value of the error and integrating it over time. In various embodiments, the integration can be performed by a leaky integrator. In various embodiments, the leaky integrator can be implemented by a low pass filter. This integrated value is referred to herein as the absolute integrated error. The absolute integrated error rises while the control system is not at target (e.g., target voltage, current or power) and goes to zero when on target. It has been found that the absolute integrated error signal of the generator control system is correlated with the presence of an arc that should be extinguished. In particular, arc behavior causes rapid changes in the impedance presented to the generator 300, and it is more difficult for the generator to track these rapid changes, thereby causing the absolute integrated error to rise during sustained arcing to metal.

At step 1202, the generator provides electrical treatment energy to the instrument based on user settings. At step 1204, the generator performs control feedback to achieve the user settings. At step 1206, the generator accesses the absolute integrated error signal from the control feedback. At step 1208, the generator determines that an arc is an arc to be extinguished based on the absolute integrated error being greater than a threshold value. And at step 1210, the generator controls the electrical treatment energy based on determining that an arc is an arc be extinguished. In various embodiments, the control at step 1210 can include decreasing the electrical treatment energy for a predetermined time duration.

Accordingly, described here are systems and methods for controlling electrical treatment energy to determine that an arc is an arc that should be extinguished. The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

The systems and methods described herein utilize one or more controllers to receive information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

The controller(s) may implement methods, programs, algorithms or codes using a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. An electrosurgical generator for controlling electrical treatment energy provided to an instrument, the generator comprising:
    one or more processors; and
    at least one memory having stored thereon instructions which, when executed by the one or more processors, cause the generator to:
        provide the electrical treatment energy to the instrument based on an indicated electrical energy level;
        access at least one of: voltage signal values over time relating to voltage of the electrical treatment energy or current signal values over time relating to current of the electrical treatment energy;
        determine a first normalized change in peak-to-peak voltage;
        determine a second normalized change in peak-to-peak voltage;
        determine that an arc generated by the instrument is an arc to be extinguished when:
            the first normalized change in peak-to-peak voltage is greater than a threshold value and an impedance of the arc is less than a first impedance threshold; or
            the second normalized change in peak-to-peak voltage is greater than a second threshold value and the impedance of the arc is less than a second impedance threshold; and
        control the electrical treatment energy based on determining that the arc is an arc to be extinguished.

2. The electrosurgical generator of claim 1, wherein the threshold value changes corresponding to changes in the indicated electrical energy level.

3. The electrosurgical generator of claim 1, wherein at least one of the first or second normalized changes in peak-to-peak voltage is a ratio of a magnitude of change in peak-to-peak voltage of the electrical treatment energy over one of: RMS voltage of the electrical treatment energy, RMS current of the electrical treatment energy, or average power of the electrical treatment energy, such that the threshold value does not change for changes in the indicated electrical energy level.

4. The electrosurgical generator of claim 1, wherein the instructions, when executed by the one or more processors, further cause the generator to determine that the arc is an arc to be extinguished based on a normalized change in peak-to-peak current of the electrical treatment energy over time being greater than the threshold value, wherein the normalized change in peak-to-peak current is a ratio of a magnitude of change in peak-to-peak current of the electrical treatment energy over one of: RMS voltage of the electrical treatment energy, RMS current of the electrical treatment energy, or average power of the electrical treatment energy, such that the threshold value does not change for changes in the indicated electrical energy level.

5. The electrosurgical generator of claim 1, wherein the instructions, when executed by the one or more processors, further cause the generator to:

determine a peak-to-peak voltage at a first time as a difference between a positive voltage peak and a negative voltage peak of the electrical treatment energy at the first time;
determine a peak-to-peak voltage at a second time as a difference between a positive voltage peak and a negative voltage peak of the electrical treatment energy at a second time, the second time being after the first time;
determine a change in peak-to-peak voltage as an absolute value of a difference between the peak-to-peak voltage at the first time and the peak-to-peak voltage at the second time;
determine an RMS voltage of the electrical treatment energy and an RMS current of the electrical treatment energy for the second time;
determine the first normalized change in peak-to-peak voltage as a ratio of the change in peak-to-peak voltage over the RMS voltage; and
determine the second normalized change in peak-to-peak voltage as a ratio of the change in peak-to-peak voltage over the RMS current.

6. The electrosurgical generator of claim 1, wherein the instructions, when executed by the one or more processors, further cause the generator to determine that the arc is an arc to be extinguished based on a crest factor of the electrical treatment energy being greater than the threshold value.

7. The electrosurgical generator of claim 1, wherein the instructions, when executed by the one or more processors, further cause the generator to determine that the arc is an arc to be extinguished based on an amount of variation in a crest factor of the electrical treatment energy over time being greater than the threshold value.

8. The electrosurgical generator of claim 7, wherein the instructions, when executed by the one or more processors, further cause the generator to:
determine voltage crest factor values over time based on a ratio of one of positive voltage peak or negative voltage peak of the electrical treatment energy over an RMS value of the electrical treatment energy;
determine current crest factor values over time based on a ratio of one of positive current peak or negative current peak of the electrical treatment energy over an RMS value of the electrical treatment energy;
high-pass filter the voltage crest factor values to provide filtered voltage crest factor values;
high-pass filter the current crest factor values to provide filtered current crest factor values;
combine absolute values of the filtered voltage crest factor values with absolute values of the filtered current crest factor values to provide the combined crest factor values; and
low-pass filter the combined crest factor values to provide the amount of variation in the voltage crest factor values and the current crest factor values.

9. An electrosurgical system, comprising:
an instrument; and
an electrosurgical generator that includes:
one or more processors, and
at least one memory having stored thereon instructions which, when executed by the one or more processors, cause the generator to:
provide electrical treatment energy to the instrument based on an indicated electrical energy level;
access at least one of: voltage signal values over time relating to voltage of the electrical treatment energy or current signal values over time relating to current of the electrical treatment energy;
determine a change in peak-to-peak voltage over time;
determine a first normalized change in peak-to-peak voltage;
determine a second normalized change in peak-to-peak voltage;
determine whether an arc generated by the instrument is an arc to be maintained or an arc to be extinguished based on a threshold value and at least one of: the voltage signal values or the current signal values;
determine that the arc is an arc to be extinguished when:
the first normalized change in peak-to-peak voltage is greater than the threshold value and an impedance of the arc is less than a first impedance threshold; or
the second normalized change in peak-to-peak voltage is greater than a second threshold value and the impedance of the arc is less than a second impedance threshold; and
control the electrical treatment energy based on determining that the arc is an arc to be extinguished.

10. The electrosurgical system of claim 9, wherein the instructions, when executed by the one or more processors, cause the generator to determine an RMS voltage of the electrical treatment energy and an RMS current of the electrical treatment energy, wherein the first normalized change in peak-to-peak voltage is determined as a ratio of the change in peak-to-peak voltage over the RMS voltage and the second normalized change in peak-to-peak voltage is determined as a ratio of the change in peak-to-peak voltage over the RMS current.

11. An electrosurgical generator, comprising:
a processor; and
a memory having stored thereon instructions which, when executed by the processor, cause the generator to:
generate electrosurgical energy;
access voltage signal values over time;
determine a first normalized change in peak-to-peak voltage;
determine a second normalized change in peak-to-peak voltage;
control generating of the electrosurgical energy to extinguish an arc generated by an electrosurgical instrument coupled to the electrosurgical generator based on a determination that:
the first normalized change in peak-to-peak voltage is greater than a first threshold value and an impedance of the arc is less than a first impedance threshold; or
the second normalized change in peak-to-peak voltage is greater than a second threshold value and the impedance of the arc is less than a second impedance threshold.

12. The electrosurgical generator of claim 11, wherein the instructions, when executed by the processor, cause the electrosurgical generator to determine an RMS voltage of the electrosurgical energy and an RMS current of the electrosurgical energy, wherein the first normalized change in peak-to-peak voltage is determined as a ratio of the change in peak-to-peak voltage over the RMS voltage and the second normalized change in peak-to-peak voltage is determined as a ratio of the change in peak-to-peak voltage over the RMS current.

13. The electrosurgical generator of claim 11, wherein the voltage signal values relate to a voltage of the electrosurgical energy.

14. The electrosurgical generator of claim 11, wherein the instructions, when executed by the processor, cause the electrosurgical generator to access current signal values over time relating to a current of the electrosurgical energy.

15. The electrosurgical generator of claim 11, wherein the instructions, when executed by the processor, cause the electrosurgical generator to provide the electrosurgical energy to the electrosurgical instrument coupled to the electrosurgical generator.

16. The electrosurgical generator of claim 11, wherein the instructions, when executed by the processor, cause the electrosurgical generator to control generating of the electrosurgical energy to extinguish the arc based on a crest factor of the electrosurgical energy being greater than the first threshold value.

17. The electrosurgical generator of claim 11, wherein the instructions, when executed by the processor, cause the electrosurgical generator to control generating of the electrosurgical energy to extinguish the arc based on an amount of variation in a crest factor of the electrosurgical energy over time being greater than the first threshold value.

18. The electrosurgical generator of claim 11, wherein the first threshold value changes in accordance with changes in a level at which the electrosurgical energy is generated.

* * * * *